United States Patent
Segawa et al.

(10) Patent No.: US 8,764,639 B2
(45) Date of Patent: Jul. 1, 2014

(54) CAPSULE MEDICAL APPARATUS WITH PROJECTIONS AND BODY-CAVITY OBSERVATION METHOD

(75) Inventors: Hidetake Segawa, Tokyo (JP); Hironobu Takizawa, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 556 days.

(21) Appl. No.: 12/983,836

(22) Filed: Jan. 3, 2011

(65) Prior Publication Data

US 2011/0098534 A1 Apr. 28, 2011

Related U.S. Application Data (62) Division of application No. 11/701,769, filed on Feb. 2, 2007, now abandoned.

(51) Int. Cl.
*A61B 1/04* (2006.01)
*A61B 1/00* (2006.01)
*A61B 1/045* (2006.01)

(52) U.S. Cl.
CPC .............. *A61B 1/041* (2013.01); *A61B 1/045* (2013.01)
USPC ............ 600/128; 600/109; 600/117; 600/118

(58) Field of Classification Search
USPC .................. 600/128, 109, 117, 118, 160, 179
See application file for complete search history.

(56) References Cited

U.S. PATENT DOCUMENTS

| 7,083,579 B2* | 8/2006 | Yokoi et al. ................... 600/593 |
| 7,553,276 B2 | 6/2009 | Iddan |
| 7,637,864 B2* | 12/2009 | Yokoi et al. ................... 600/114 |
| 2003/0020810 A1 | 1/2003 | Takizawa et al. |
| 2003/0181788 A1 | 9/2003 | Yokoi et al. |
| 2003/0214579 A1 | 11/2003 | Iddan |
| 2003/0216622 A1* | 11/2003 | Meron et al. .................. 600/300 |
| 2005/0004474 A1 | 1/2005 | Iddan |
| 2005/0043583 A1* | 2/2005 | Killmann et al. ............. 600/109 |

FOREIGN PATENT DOCUMENTS

| JP | 2003-275170 A | 9/2003 |
| JP | 2003-275171 A | 9/2003 |
| WO | WO 02/054932 A2 | 7/2002 |
| WO | WO 02/095351 A2 | 11/2002 |

(Continued)

OTHER PUBLICATIONS

European Office Action dated Jun. 18, 2012 from corresponding European Patent Application No. EP 08 710 952.6.

(Continued)

*Primary Examiner* — Alireza Nia
(74) *Attorney, Agent, or Firm* — Scully, Scott, Murphy & Presser, P.C.

(57) ABSTRACT

Provided is a capsule medical apparatus including a capsule body, a control member, and an observing member. The capsule body is to be introduced into a lumen of a subject. The control member controls a movement of the capsule body in the lumen by a flow of a fluid introduced in the lumen. The observing member is fixed inside the capsule body and observes a direction of the flow of the fluid and a direction different from the flow of the fluid according to the movement of the capsule body.

9 Claims, 10 Drawing Sheets

(56) References Cited

FOREIGN PATENT DOCUMENTS

| | | |
|---|---|---|
| WO | WO 03/011103 A2 | 2/2003 |
| WO | WO 2004/041068 A2 | 5/2004 |
| WO | WO 2005/060348 A2 | 7/2005 |
| WO | WO 2005/062717 A2 | 7/2005 |
| WO | WO 2005/112460 A2 | 11/2005 |
| WO | WO 2006/057443 A1 | 6/2006 |

OTHER PUBLICATIONS

International Search Report and Written Opinion dated May 29, 2008.

U.S. Office Action dated Aug. 2, 2010.

Japanese Office Action dated May 8, 2012 from corresponding Japanese Patent Application No. 2009-524834.

* cited by examiner

FLUID FLOW

FIG.14C

CAPSULE MEDICAL APPARATUS WITH PROJECTIONS AND BODY-CAVITY OBSERVATION METHOD

CROSS-REFERENCE TO RELATED APPLICATIONS

This application is a Divisional Application of U.S. application Ser. No. 11/701,769 filed on Feb. 2, 2007, the entire contents of which is incorporated herein by reference.

BACKGROUND OF THE INVENTION

1. Field of the Invention

The present invention relates to a capsule medical apparatus such as a capsule endoscope for traveling in a lumen with a liquid such as water, which is introduced into a subject, to observe inside the lumen and a body-cavity observation method.

2. Description of the Related Art

Recently, in a field of endoscopes, a capsule endoscope having an imaging function and a radio communication function has been appearing. This capsule endoscope includes a structure for displacing along with peristaltic movement in an internal organ (in a lumen) such as the esophagus, stomach and small intestine and sequentially taking images with its imaging function until it is naturally discharged from the body of the subject, after swallowed by the subject through his or her mouth for the observation (examination).

WO 02/95351 discloses a technique suited for observing the large intestine, in which the specific gravity of the capsule endoscope is set as same as that of the liquid therearound or 1 which is same as that of water so that, when a subject swallows the capsule endoscope with the liquid, the capsule endoscope floats in the liquid and travels quickly in the body-cavity to the large intestine. When the capsule endoscope is attached to the wall surface of the body-cavity, only close narrow area is imaged; however, according to WO 02/95351, since the capsule endoscope floats in the liquid to observe, an observing field is maintained and every part can be observed.

Regarding observations of inside hollow organs such as the large intestine with the use of such a capsule endoscope, an entire of the lumen may be needed to be observed in some cases and a particular portion such as a polyp (lumen wall) may be needed to be observed in other cases. In order to meet such demands, for example, WO 03/11103 discloses a capsule endoscope having at least one illumination source, at least one imaging sensor, and at least two optic systems. Further, WO 02/54932 discloses a capsule endoscope having at least one imaging device and an optic system including a plurality of optical paths. According to WO 03/11103 and WO 02/54932, the capsule endoscope is capable of imaging the lumen not only in the axial direction of the lumen but also in an inner wall direction of the lumen in the hollow organ.

However, according to the capsule endoscope of WO 03/11103 and WO 02/54932, the system depends on the structure of the imaging optical system in the capsule endoscope and in order to optimize imaging direction to perform a proper observation in the lumen in its axial direction and the inner wall direction, more optic systems or optical paths are required to be set. Thus, the structure becomes more complex and enlarged so that the proper size of the capsule endoscope to be introduced into a subject cannot be maintained.

SUMMARY OF THE INVENTION

A capsule medical apparatus according to one aspect of the present invention includes a capsule body to be introduced into a lumen of a subject; a control member controlling a movement of the capsule body in the lumen by a flow of a fluid introduced in the lumen; and an observing member fixed inside the capsule body and observing a direction of the flow of the fluid and a direction different from the flow of the fluid according to the movement of the capsule body.

A body-cavity observation method according to another aspect of the present invention includes the steps of: ingesting a capsule medical apparatus; ingesting a fluid having a specific gravity which is substantially same as that of the capsule medical apparatus; controlling, by the capsule medical apparatus, movement in a lumen by a flow of the fluid; observing, by the capsule medical apparatus, a direction of the flow of the fluid; and observing, by the capsule medical apparatus, a direction different from the direction of the flow of the fluid.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Embodiments of a capsule medical apparatus and a body-cavity observation method according to the present invention will be described with reference to the drawings. The embodiments describe examples of the present invention applied to a capsule endoscope as a capsule medical apparatus. It will be appreciated that the present invention is not limited to the following embodiments and can be implemented with modifications within the spirit of the present invention.

Figure 1:
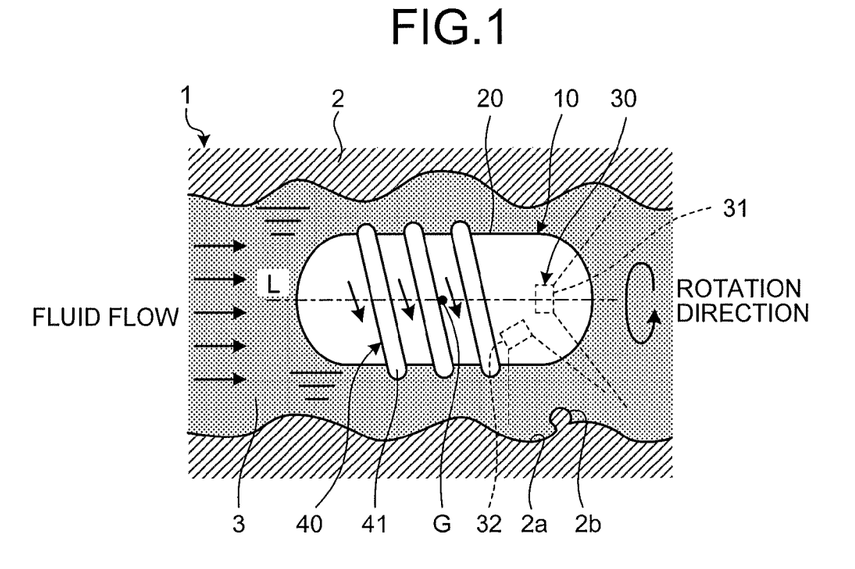
FIG. 1 is a schematic block diagram showing a use example of a capsule endoscope according to a first embodiment of the present invention.

FIG. 1 is a schematic block diagram showing a use example of a capsule endoscope according to a first embodiment of the present invention. The capsule endoscope 10 of the first embodiment includes a capsule body 20 insertable into a lumen of a subject 1 to be tested, an observing member 30 installed in the capsule body 20, other installed elements such as a radio transmission unit, a battery, an image processing unit, which are not shown, and a rotary guide member 40 disposed on outer face of the capsule body 20.

The capsule body 20 is made in a size capable of being swallowed by the subject 1 through his or her mouth into a body cavity of the subject 1. The capsule body 20 is formed in a domed capsule shape, in which ends of hemispherical domes are integrated by a cylindrical member therebetween and the direction connecting the ends of the hemispherical domes represents a longitudinal direction.

Here, the capsule endoscope 10 of the first embodiment is configured to propel in the lumen 2 of the subject 1, for example, the large intestine, as floating in a fluid 3 that is introduced in the lumen 2. The capsule body 20, which includes installed elements such as the observing member 30, is configured to have a specific gravity that is substantially one with respect to the fluid 3, substantially the same as the fluid 3. The fluid 3 is a fluid, which is capable of being swallowed by the subject 1 through his or her mouth and is clear to the wavelength of a light source used by the observing member 30 for imaging. In the first embodiment, drinkable water having specific gravity close to one is used as an example of the fluid 3. A gravity center G of the capsule body 20 containing the observing member 30 and other elements is set as the center of the capsule body 20 (the center on the longitudinal axis L passing through the center of the cylinder).

Further, the observing member 30 is an imaging member for imaging an image of the inside of the lumen and, according to the first embodiment, is composed of first and second imaging members 31, 32 which are fixed at a position one-sided with respect to the longitudinal axial direction in the capsule body 20. The first imaging member 31, which is not shown, includes a light source for illuminating an imaging region, a solid-state imaging device such as CCD or CMOS imager for receiving catoptric light from the imaging region generated by the illuminating light of the light source to image the inside of the lumen, and an imaging optic system such as an imaging lens for producing an optical image of the imaging region to the solid-state imaging device. As shown with dashed lines in FIG. 1, the first imaging member 31 is disposed so as to provide an imaging field in the longitudinal axial direction of the capsule body 20. Further, the second imaging member 32, which is not shown, includes a light source for illuminating an imaging region, a solid-state imaging device such as CCD or CMOS imager for receiving catoptric light from the imaging region generated by the illuminating light of the light source to image the inside of the lumen, and an imaging optic system such as an imaging lens for producing an optical image of the imaging region to the solid-state imaging device. As shown with the dashed lines in FIG. 1, the second imaging member 32 is disposed so as to provide an imaging field in a direction oblique to the longitudinal axis direction of the capsule body 20. Here, the first imaging member 31 is set to be a far focus to focus on a distant point and the second imaging member 32 is set to be a near focus to focus on a close point. The imaging field of the second imaging member 32 may be in a horizontal direction with respect to the vertical axial direction of the capsule body 20. Here, the capsule body 20 includes a member having clearness or translucency at least at regions corresponding to the imaging fields of the first and second imaging members 31, 32.

Further, the rotary guide member 40 is configured to work as a control member for controlling movement of the capsule body 20 in the lumen 2, which is moved by the flow of the fluid 3 introduced into the lumen 2. According to the first embodiment, the rotary guide member 40 is configured to rotate the capsule body 20 with the flow of the fluid 3 about the longitudinal axis of the capsule body 20 in a circumferential direction. The rotary guide member 40 is composed of a spiral member formed of a continuous projection 41 with projection amount which is capable of interfering the flow of the fluid 3, spirally formed around the outer surface of the capsule body 20. The cross-sectional shape of the projection 41 may be formed in a hemicycle or a rectangle shape. Further, the interval of the spiral, the number of the spiral, the angle of the spiral or the like of the projection 41 can be set arbitrarily.

An image processing unit which is installed in the capsule body 20, which is not shown, provides necessary processing on the images of the inside of the lumen taken by the first and second imaging members 31, 32. A radio transmission unit, which is not shown, radio-outputs lumen image data which has been subjected to necessary processing by the image processing unit to a receiver (not shown) or the like disposed outside the subject 1. A battery, which is not shown, supplies necessary power to an electrical drive unit such as the light source or solid-state imaging device in the capsule body 20.

Next, an observation of inside of the lumen 2, for example, the large intestine, with the use of the capsule endoscope 10 of the first embodiment will be described. Basically, the capsule endoscope 10 and the fluid 3 are swallowed by the subject 1 to substantially fill the lumen 2 such as the large intestine as an observed portion in the subject 1 with the fluid 3 so that the capsule endoscope 10 travels as floating in the fluid 3. Then the inside image of the lumen is taken by the first and second imaging members 31, 32 to observe the lumen. The capsule endoscope 10 and the liquid 3 may be swallowed at the same time or may be swallowed in any order.

Here, as shown by arrows in FIG. 1, the fluid 3 introduced in the lumen 2 flows along the axis of the lumen 2 toward an exit of the lumen. When the capsule endoscope 10 is in such a flow of the fluid 3, since the capsule body 20 has the rotary guide member 40 of the spirally formed projection 41 on the outer face and the rotary guide member 40 interferes the flow of the fluid 3, the capsule endoscope 10 is controlled to move along the flow as rotating in the circumferential direction about the longitudinal axis L. The first and second imaging members 31, 32 take images inside the lumen 2 in such movements of the capsule body 20. In other words, the first imaging member 31 takes images of the lumen 2, as rotating, in front (or back) in the axial direction that is the direction of the flow of the fluid 3. The second imaging member 32 sequentially takes images of an internal surface 2a of the lumen 2, which is located in different direction from the flow of the fluid 3, as moving around therein. Further, since the focus position of the first imaging member 31, which images the lumen 2 in the axial direction, is set at a long distance, a far focused and fine image of the inside of the entire lumen can be obtained. Since the focus position of the second imaging member 32, which images the internal surface 2a as moving around therein, is set at a short distance, a near focused and fine internal surface image can be obtained and a particular portion such as a polyp 2b can surely be observed.

As described above, according to the capsule endoscope 10 of the first embodiment, the observing fields in the lumen 2 can be dynamically changed to be optimized by controlling the capsule body 20 to move as rotating in a circumferential direction with the use of the flow of the fluid 3. With this structure, the entire parts in the lumen 2 can surely be observed without complicating the structure of an observing member (imaging member), which is to be installed in the capsule body 20. Further, according to the capsule endoscope 10 of the first embodiment, the gravity center G is set at the substantially center of the capsule body 20 and the specific gravity with respect to the fluid 3 is set as substantially one. Accordingly, the capsule body 20 is in a mobile state and rotatable smoothly in the circumferential direction when the rotary guide member 40 interferes the flow of the fluid 3. With this structure, the above described observing operation can be certainly performed.

Figure 2:
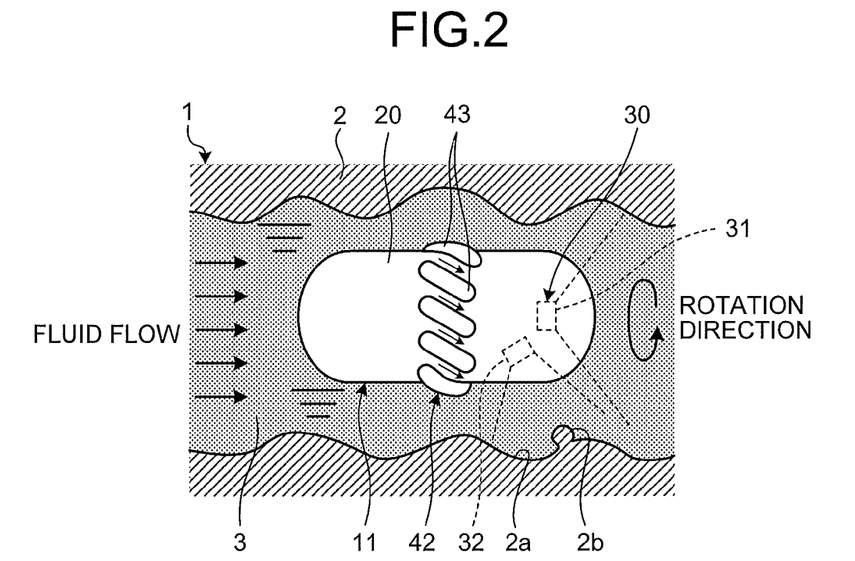
FIG. 2 is a schematic block diagram showing a use example of a capsule endoscope according to a first modification.

FIG. 2 is a schematic block diagram showing a use example of the capsule endoscope according to a first modification. According to a capsule endoscope 11 of the first modification, a rotary guide member 42 is formed with a plurality of noncontiguous projections 43 so as to form an intermissive spiral shape. In this way, the rotary guide member 42 may be formed in an intermissive spiral shape with the noncontiguous projections 43 if the rotary guide member 42 is configured to interface the flow of the fluid 3 to rotate the capsule body 20 in a circumferential direction about the longitudinal axis L. Such a rotary guide member 42 may be formed more easily than the rotary guide member of the continuous projection 41.

The rotary guide member is not limited to what is formed spirally with the projections 41, 43 and may be, for example, formed with a recess, which is spirally formed on the outer surface of the capsule body 20 to interface the flow of the fluid 3. Further, according to the first embodiment and the first modification, the observing member 30 (the first and second imaging members 31, 32) is not limited to be disposed only at one end in the capsule body 20 and the observing members 30 may be fixed at both ends as a compound-eye-type structure. In addition, the first imaging member 31 and the second imaging member 32 may be arranged at different ends.

Figure 3:
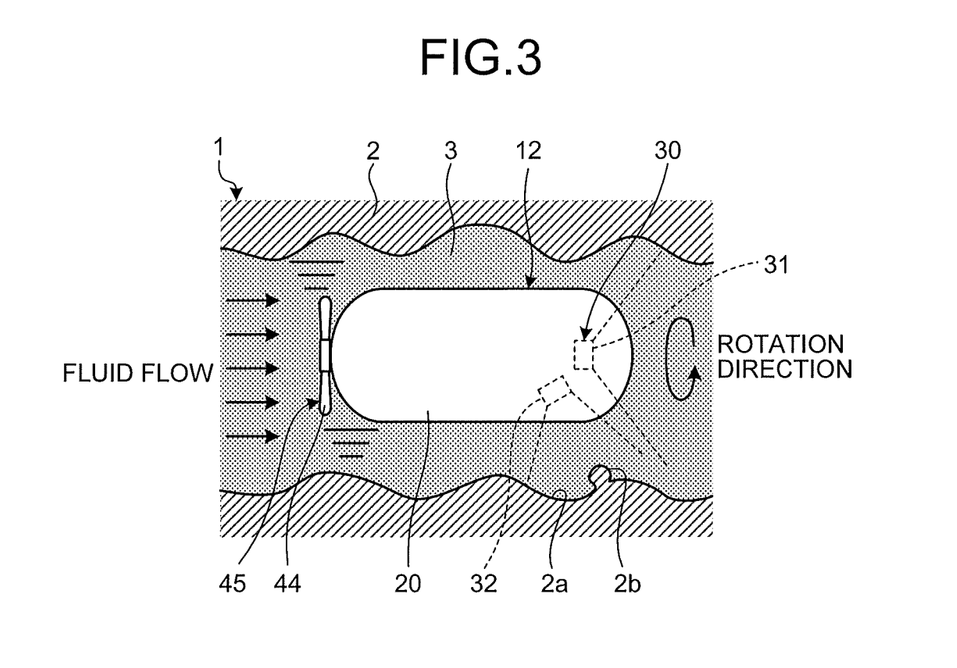
FIG. 3 is a schematic block diagram showing a use example of a capsule endoscope according to a second modification.
Figure 4:
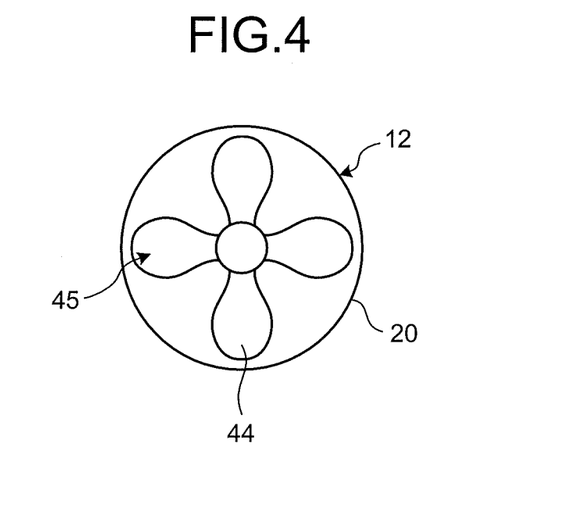
FIG. 4 is a schematic rear view of the capsule endoscope.

FIG. 3 is a schematic block diagram showing a use example of a capsule endoscope according to a second modification and FIG. 4 is a schematic rear view of the capsule endoscope. A capsule endoscope 12 according to the second modification includes a propeller 44 as a rotary guide member 45, which is integrally provided on the outer surface of a rear portion (the portion where the observing member 30 is not provided) of the capsule body 20. When the capsule endoscope 12 having such structure receives a flow of the fluid 3 in the lumen 2, the propeller 44 as the rotary guide member 45 rotates as interfering the flow of the fluid 3 so that the capsule body 20 moves forward in the lumen 2 as rotating, together with the propeller 44, in a circumferential direction about the longitudinal axis L. Accordingly, same as the case of the first embodiment, the inside of the lumen 2 may surely be observed.

Figure 5:
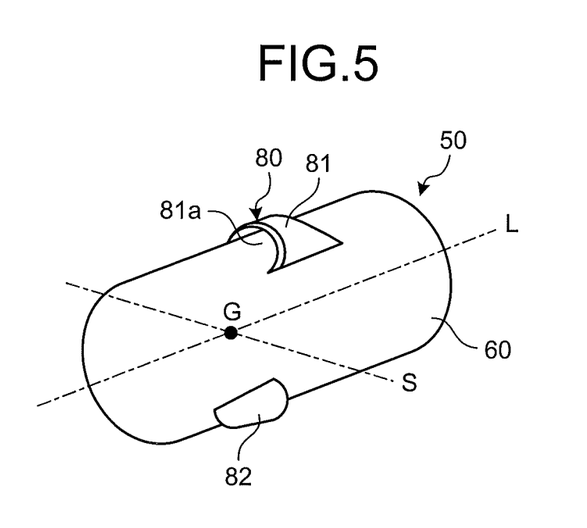
FIG. 5 is a schematic perspective view showing the capsule endoscope according to a second embodiment of the present invention.
Figure 6:
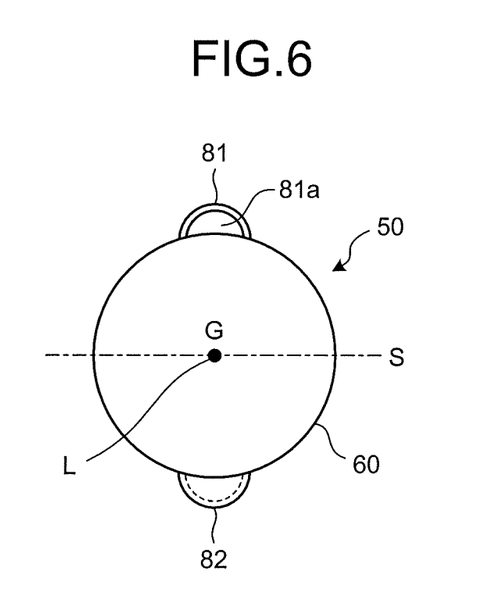
FIG. 6 is a rear view of the capsule endoscope in FIG. 5.

Next, a capsule endoscope according to a second embodiment of the present invention will be described. FIG. 5 is a schematic perspective view showing the capsule endoscope according to the second embodiment, FIG. 6 is a rear view of the capsule endoscope in FIG. 5, and FIGS. 7A, 7B and 7C are schematic block diagrams showing a use example of the capsule endoscope. A capsule endoscope 50 according to the second embodiment includes a capsule body 60 which is insertable into a lumen of a subject 1, an observing member 70 installed in the capsule body 60, other installed elements, which are not shown, such as a radio transmission unit, a battery or an image processing unit, and a rotary guide member 80 disposed on the outer surface of the capsule body 70.

The capsule body 60 is basically same as the capsule body 20. The capsule body 60 is made in a size capable of being swallowed by the subject 1 through his or her mouth into a cavity. The capsule body 60 is formed in a domed capsule shape, in which ends of hemispherical domes are integrated by a cylindrical member therebetween and the direction connecting the ends of the hemispherical domes is a longitudinal direction.

Here, the capsule endoscope 50 of the second embodiment moves in a lumen 2, for example, the large intestine of the subject 1, as floating in the fluid 3 introduced into the lumen 2. The capsule body 60, which includes elements such as the observing member 70 therein, is configured to have a specific gravity that is substantially one with respect to the fluid 3, substantially the same as that of the fluid 3. The fluid 3 is a liquid, which is capable of being swallowed by the subject 1 through his or her mouth and is clear to the wavelength of a light source used by the observing member 30 for imaging. In the second embodiment, drinkable water having specific gravity close to one is used as an example of the fluid 3. The gravity center G of the capsule body 60 containing the observing member 30 and other elements is set as the center of the capsule body 60 (the center on the longitudinal axis L passing through the center of the cylinder).

Further, the observing member 70 is an imaging member for imaging an image of the inside of the lumen and, according to the second embodiment, is composed of an imaging member 71 that is fixed at a position one-sided with respect to the longitudinal axial direction in the capsule body 60. The imaging member 71, which is not shown, includes a light source for illuminating an imaging region, a solid-state imaging device such as CCD or CMOS imager for receiving catoptric light from the imaging region generated by the illuminating light of the light source to image the inside of the lumen, and an imaging optical system such as an imaging lens for producing an optical image of the imaging region to the solid-state imaging device. As shown with dashed lines in FIGS. 7A to 7C, the imaging member 71 is disposed so as to provide an imaging field in the longitudinal axial direction of the capsule body 60. Here, the capsule body 60 includes a member having clearness or translucency at least at regions corresponding to the imaging field of the imaging member 71.

Further, the rotary guide member 80 is configured to work as a control member for controlling movement of the capsule body 20 in the lumen 2, which is moved by the flow of the fluid 3 introduced into the lumen 2. According to the second embodiment, the rotary guide member 80 is configured to rotate the capsule body 60 with the flow of the fluid 3 about an axis S passing through the gravity center G of the capsule body 60 and substantially perpendicular to the longitudinal axis L in a circumferential direction. The rotary guide member 80 is composed of projections 81, 82 in a pocket form having openings 81a, 82a on the outer surface of the capsule body 60 to form a pair of one-way resistive elements. The openings 81a, 82a are opened along the longitudinal axial direction and toward the center portion of the capsule body 60. These pocket projections 81, 82 are disposed at a position off the center of the longitudinal axis L on the outer surface of the capsule body 60 so as to be point symmetric with respect to the gravity center G of the capsule body 60. Further, these pocket projections 81, 82 are formed symmetrically when they are divided into two pieces at a plane face including the longitudinal axis L of the capsule body 60 and disposed to be point symmetric with respect to the gravity center G of the capsule body 60. Here, the pocket projections 81, 82 work as resistive elements and generate reaction force when the openings 81a, 82a are opened toward upstream to face to the flow of the fluid 3, and, on the other hand, the pocket projections 81, 82 do not work as resistive elements when the openings 81a, 82a are opened toward downstream and does not face to the flow of the fluid 3 and have directionality to generate reaction force to the flow of the fluid 3.

Figure 7A:
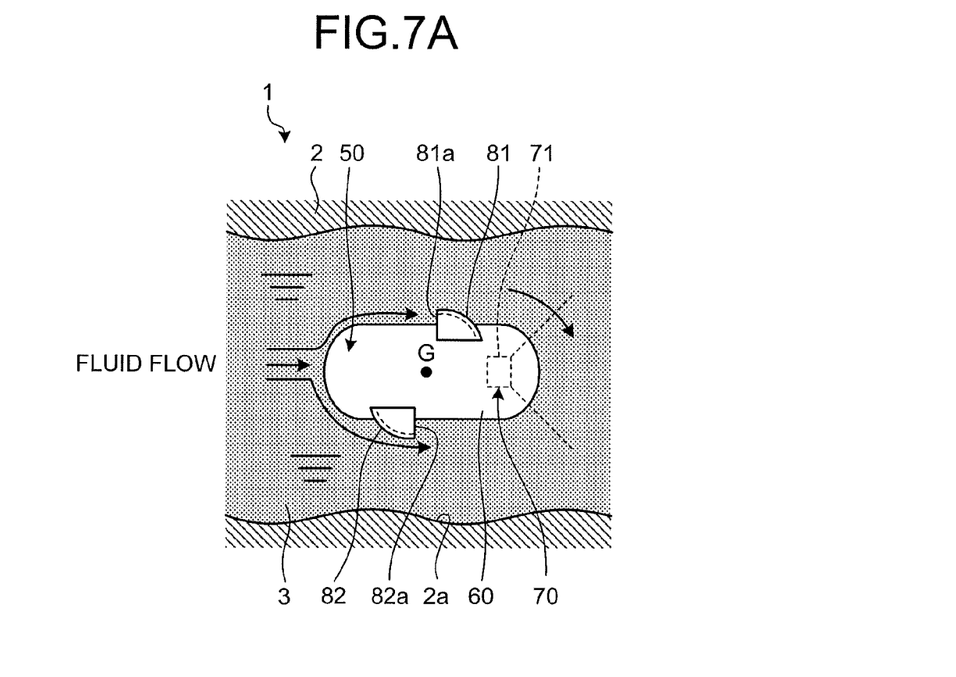
FIGS. 7A, 7B and 7C are schematic block diagrams showing a use example of the capsule endoscope.
Figure 7B:
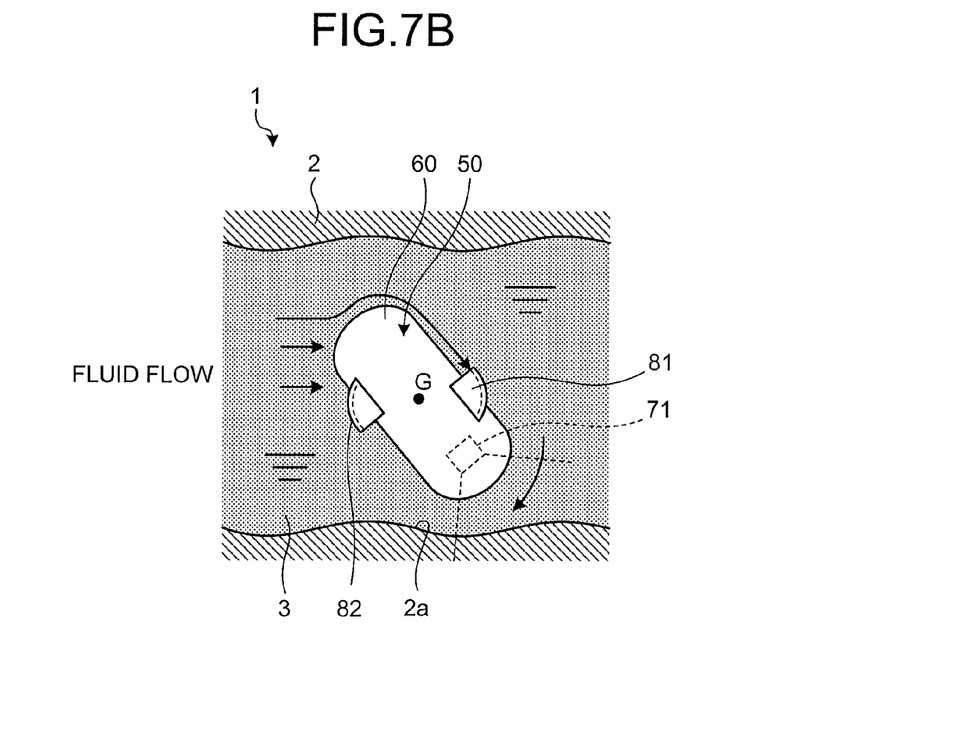
Figure 7C:
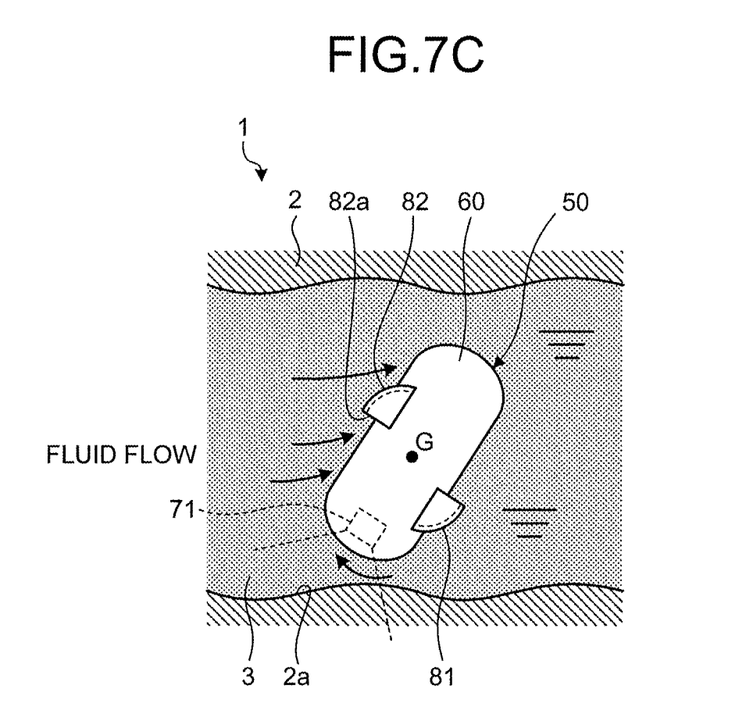

Next, an observation of inside of the lumen 2, for example, the large intestine with the use of the capsule endoscope 50 of the second embodiment will be described. Basically, the capsule endoscope 50 and the fluid 3 are swallowed from a mouth to substantially fill the lumen 2 such as the large intestine as an observed portion in the subject 1 with the fluid 3 so that the capsule endoscope 50 travels as floating in the fluid 3 while an imaging member 71 takes images of the inside of the lumen 2. The capsule endoscope 50 and the liquid 3 may be swallowed at the same time or may be swallowed in any order.

Here, as shown by arrows in FIG. 7A, the fluid 3 introduced in the lumen 2 flows toward an exit of the lumen. When the capsule endoscope 50 is in such a flow of the fluid 3, since the capsule body 60 has the rotary guide member 80 of the pocket projections 81, 82 on its outer face, one of the projection 81 or the projection 82 faces to the flow of the fluid 3 to generate a reaction force. Accordingly, the capsule body 60 is controlled to move along the flow as rotating radially about an axis S that passes through the gravity center G of the capsule body 60 and substantially perpendicular to the longitudinal axis L.

For example, as shown in FIG. 7A, when the opening 81a of the projection 81 faces to the flow of the fluid 3, the projection 81 generates an reaction force against the flow of the fluid 3 and works as a trigger to rotate the capsule body 60 in the clockwise direction about the axis S. The capsule body 60 rotates in the clockwise direction about the axis S (rolls forward) along the flow of the fluid 3, as shown in FIG. 7B. In this operation, the other projection 82 does not generate a reaction force since the opening 82a does not face to the flow. Then, when the capsule body 60 continues to rotate, as shown in FIG. 7C, the opening 82a of the other projection 82 comes to face to the flow of the fluid 3 and the projection 82 generates a reaction force against the flow of the fluid 3 to rotate the capsule body 60 in the clockwise direction about the axis S. With repeating this operation, the capsule body 60 travels forwardly in the lumen 2 as rotating about the axis S by the flow of the fluid 3.

The imaging member 71 takes images of the inside of the lumen 2 in such a movement of the capsule body 60. In other words, the imaging member 71 sequentially takes images of internal surfaces 2a of the lumen 2 at front side and back side of an axis of the lumen 2 that is the flowing direction of the fluid 3 and at different directions from the flowing direction of the fluid 3 as rotating forwardly and following the rotating trajectory. With this structure, the entire area in the lumen 2 and particular parts of the internal surface 2a can be observed.

When the flow of the fluid 3 is small, since the resistance received by the projection 81 or 82 facing to the flow becomes small, the capsule body 60 does not rotate about the axis S. Accordingly, when the flow is small, the imaging member 71 takes images in axial direction of the lumen 2 and, when the flow has certain strength or more, the imaging member 71 observes particular portion of the internal surface 2a. When the flow of the fluid 3 has a periodicity, both entire images and partial images can be observed more efficiently.

As described above, according to the capsule endoscope 50 of the second embodiment, the capsule body 60 is moved as rotating radially about the axis S (rotating forwardly) with the use of the flow of the fluid 3. With this structure, an observing field in the lumen 2 can dynamically be changed to be optimized even when the capsule endoscope 50 has a structure including a single observing member 70 for a direct view.

Thus, the entire area in the lumen 2 can be surely observed without complicating the structure of an observing member (imaging member), which is to be installed in the capsule body 60. Further, according to the capsule endoscope 50 of the second embodiment, the gravity center G is set at the substantially center of the capsule body 60 and the specific gravity with respect to the fluid 3 is set as substantially one. Accordingly, the capsule body 60 is in a mobile state and rotatable in the radial direction about the axis S smoothly when the pocket projections 81, 82 constituting the rotary guide member 80 alternately face to the flow of the fluid 3. With this structure, the above described observing operation can certainly be performed.

Figure 8:
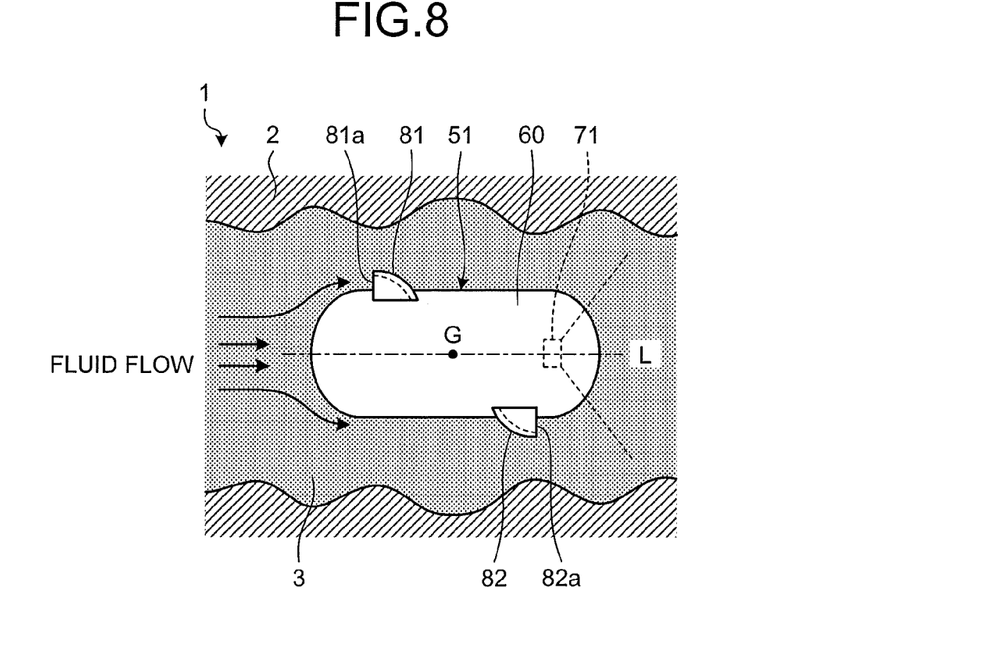
FIG. 8 is a schematic block diagram showing a use example of a capsule endoscope according to a third modification.

FIG. 8 is a schematic block diagram showing a use example of a capsule endoscope according to a third modification. A capsule endoscope 51 of the third modification has a pair of pocket projections 81, 82 constituting a rotary guide member 80 in which openings 81a, 82a are opened toward ends along the longitudinal axial direction. With the capsule endoscope 51 having the structure described in the third modification, operations and effects same as those of the second embodiment can be obtained.

Figure 9:
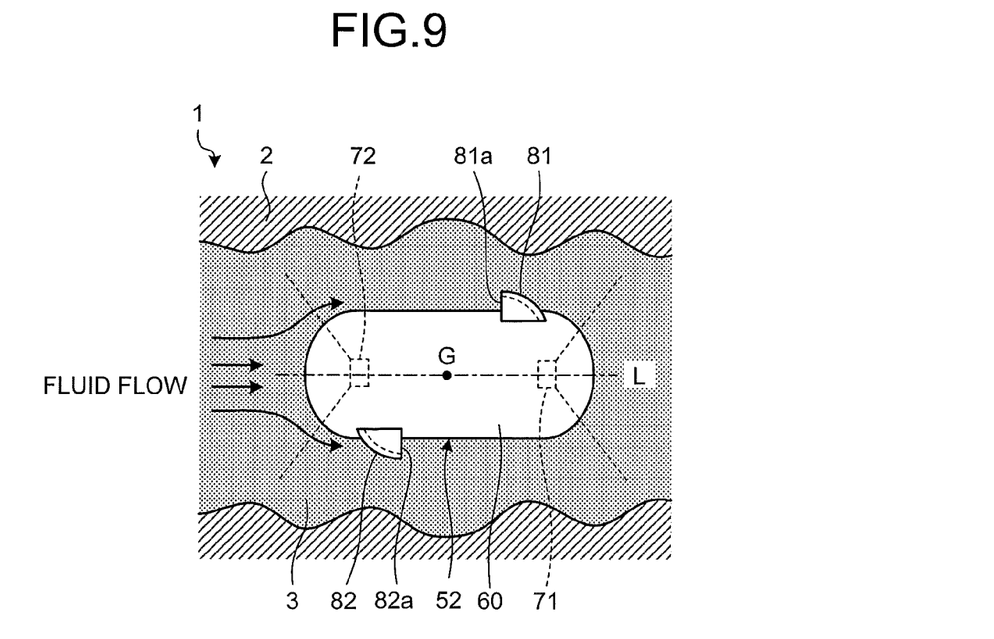
FIG. 9 is a schematic block diagram showing a use example of a capsule endoscope according to a fourth modification.

FIG. 9 is a schematic block diagram showing a use example of a capsule endoscope according to a fourth modification. A capsule endoscope 52 of the fourth modification includes an imaging member 71 as a first observing member and a second observing member 72 for forming at another imaging field in a longitudinal direction of the capsule body 60, which is fixed another end of the capsule body 60. A compound-eye-type observing member 70 is composed of the first and second imaging members 71, 72.

Here, similarly to the first imaging member 71, the second observing member 72, which is not shown, includes a light source for illuminating an imaging region, a solid-state imaging device such as CCD or CMOS imager for receiving catoptric light from the imaging region generated by the illuminating light of the light source to image the inside of the lumen, and an imaging optical system such as an imaging lens for producing an optical image of the imaging region to the solid-state imaging device. Further, the first imaging member 71 is set to be a far focus to focus on a entire image of the lumen 2 and the second imaging member 72 is set to be a near focus to observe the internal surface or the like of the lumen 2. Here, the capsule body 60 also includes a member having clearness or translucency for a region corresponding to the imaging field of the second imaging member 72.

With the capsule endoscope 52 having the structure described in the fourth modification, operations and effects same as those of the second embodiment can be obtained. Particularly, since the capsule endoscope 52 of the third modification has a compound-eye-type structure with the first and second imaging members 71, 72 having different focusing lengths, when the capsule body 60 rotates radially about the axis S by the flow of the fluid 3, the first and second imaging members 71, 72 sequentially take images in the lumen 2 as following the rotating trajectory. In this case, since the focus position of the first imaging member 71 is set at a long distance, a far focused and fine image of the inside of the entire lumen can be obtained by extracting a well-focused image from the obtained images. Further, since the focus position of the second imaging member 72 is set at a short distance, a near focused and fine internal surface image can be obtained and a particular portion such as a polyp can surely be observed by extracting a well-focused image from the obtained images.

Figure 10:
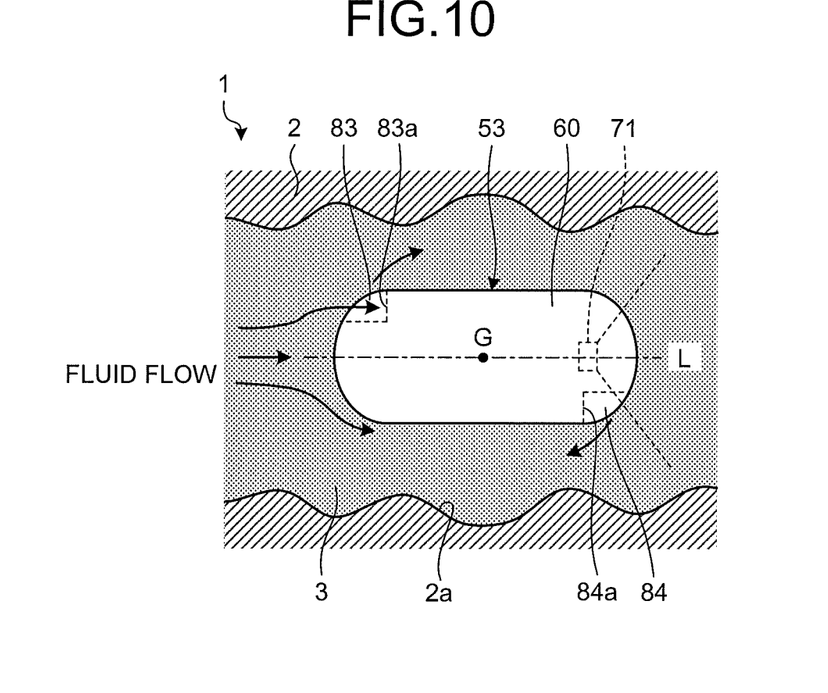
FIG. 10 is a schematic block diagram showing a use example of a capsule endoscope according to a fifth modification.
Figure 11:
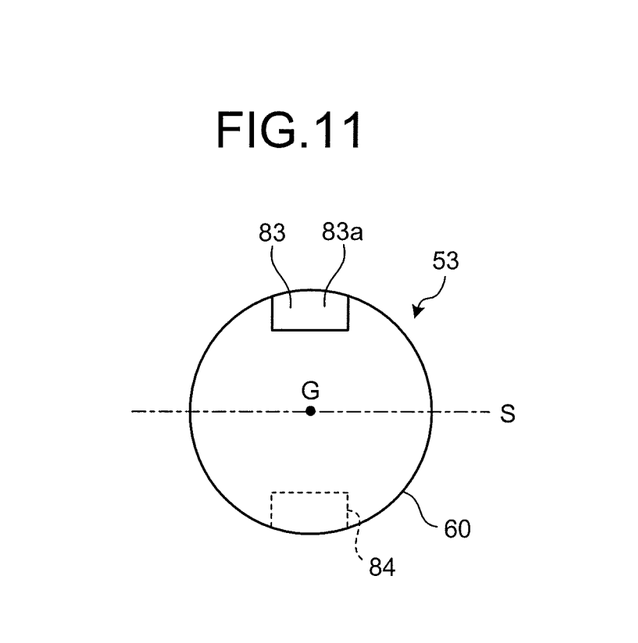
FIG. 11 is a rear view of the capsule endoscope in FIG. 10.

FIG. 10 is a schematic block diagram showing a use example of a capsule endoscope according to a fifth modification and FIG. 11 is a rear view of the capsule endoscope. A capsule endoscope 53 of the fifth modification includes a pair of grooves 83, 84 as a pair of one-way resistive elements constituting a rotary guide member 80, as substitutes for the pair of pocket projections 81, 82. The grooves 83, 84 are formed in a manner being opened near the end portions on the outer surface of the capsule body 60 along the longitudinal axial direction and toward the side of the end portions. Inner walls of the grooves 83, 84 work as fluid contact faces 83a, 84b. The grooves 83, 84 are arranged to be point symmetric with respect to the gravity center G of the capsule body 60. Further, the cross-sectional shape of the grooves 83, 84 may be triangular or U-shaped which are symmetrical when they are divided into two at a flat face including the longitudinal axis L of the capsule body 60 and arranged to be point symmetric with respect to the gravity center G.

Here, the grooves 83, 84 work as resistive elements to generate a reaction force when the fluid contact faces 83a, 84a face toward the upstream and face to the flow of the fluid 3, and the grooves 83, 84 do not work as resistive element when the fluid contact face 83a, 84a face toward the downstream and do not face to the flow of the fluid 3 and have directionality to generate reaction force to the flow of the fluid 3. With the capsule endoscope 53 having the structure described in the fifth modification, operations and effects same as those of the second embodiment can be obtained.

Figure 12:
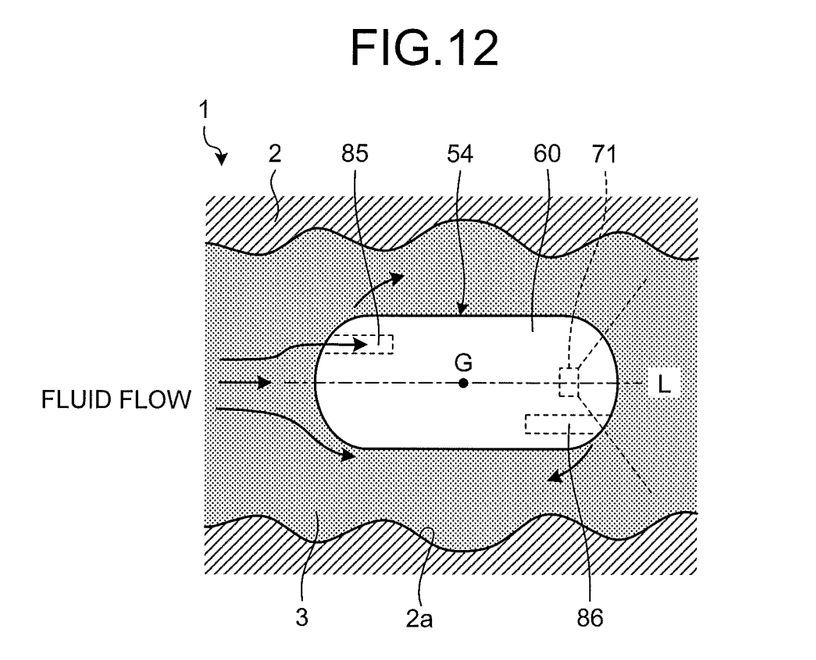
FIG. 12 is a schematic block diagram showing a use example of a capsule endoscope according to a sixth modification.
Figure 13:
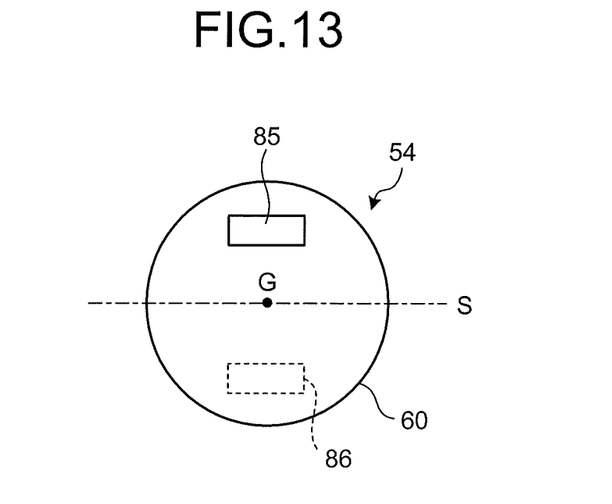
FIG. 13 is a rear view of the capsule endoscope in FIG. 12.

FIG. 12 is a schematic block diagram showing a use example of a capsule endoscope according to a sixth modification and FIG. 13 is a rear view of the capsule endoscope. A capsule endoscope 54 of the sixth modification includes a pair of holes 85, 86 as a pair of one-way resistive elements constituting a rotary guide member 80, as substitutes for the pair of pocket projections 81, 82. The holes 85, 86 are formed in a manner opened near the end portions on the outer surface of the capsule body 60 along the longitudinal axial direction and toward the side of the end portions. The holes 85, 86 are arranged to be point symmetric with respect to the gravity center G of the capsule body 60. Further, the cross-sectional shape of the holes 85, 86 may be triangular or round shape, which are symmetrical when they are divided into two at a flat face including the longitudinal axis L of the capsule body 60, and arranged to be point symmetric with respect to the gravity center G.

Here, the holes 85, 86 work as resistive elements to generate a reaction force when the openings opened toward the upstream and face to the flow of the fluid 3, and the holes 85, 86 do not work as resistive element when the openings open toward the downstream and do not face to the flow of the fluid 3 and have directionality to generate reaction force to the flow of the fluid 3. With the capsule endoscope 54 having the structure described in the sixth modification, operations and effects same as those of the second embodiment can be obtained.

Here, according to the third to sixth modifications of the second embodiment, the rotary guide member 80 is composed of a pair of one-way resistive elements formed by the pair of the pocket projections 81, 82, grooves 83, 84, or holes 85, 86. However, the rotary guide member 80 composed of a pair of one-way resistive elements in which a plurality of projections, grooves, or holes are symmetrically disposed in combination in each side may be employed.

Further, the projected resistive element may be openable and closable (projected and retracted) with respect to the outer surface of the capsule body. In other words, when the fluid 3 is still (or its flow is small), the resistive element is closed (installed in the capsule body) and when a large flow is generated, the resistive element is opened (projected) corresponding to the flow. With this structure, since projections are projected only when they are need, the capsule endoscope can be easily swallowed by the subject 1.

Figure 14A:
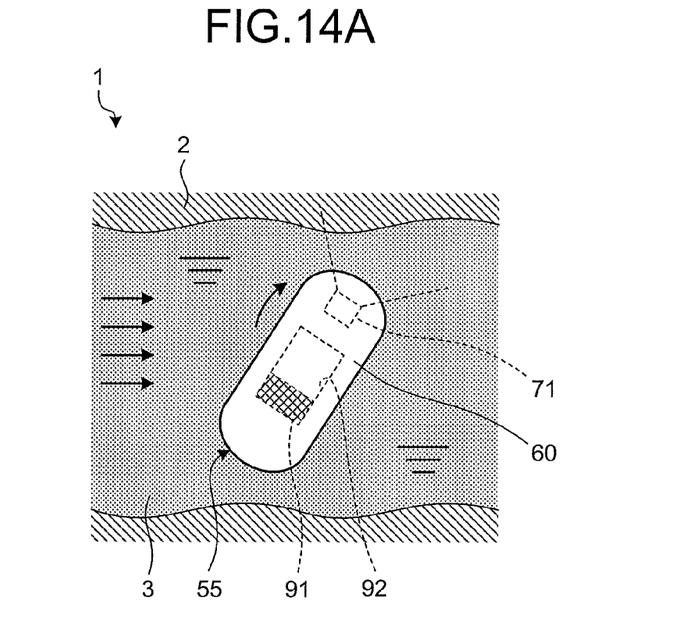
FIGS. 14A, 14B and 14C are schematic block diagrams showing a use example of a capsule endoscope according to a seventh modification.
Figure 14B:
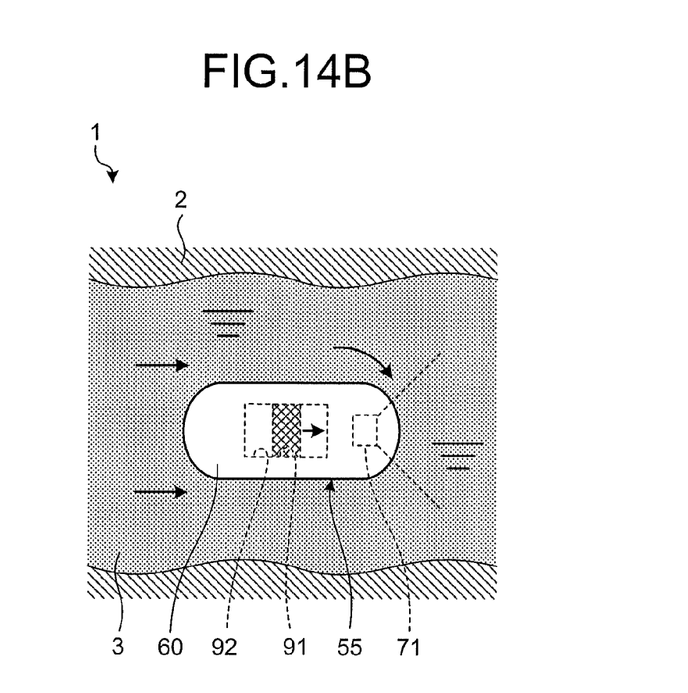
Figure 14C:
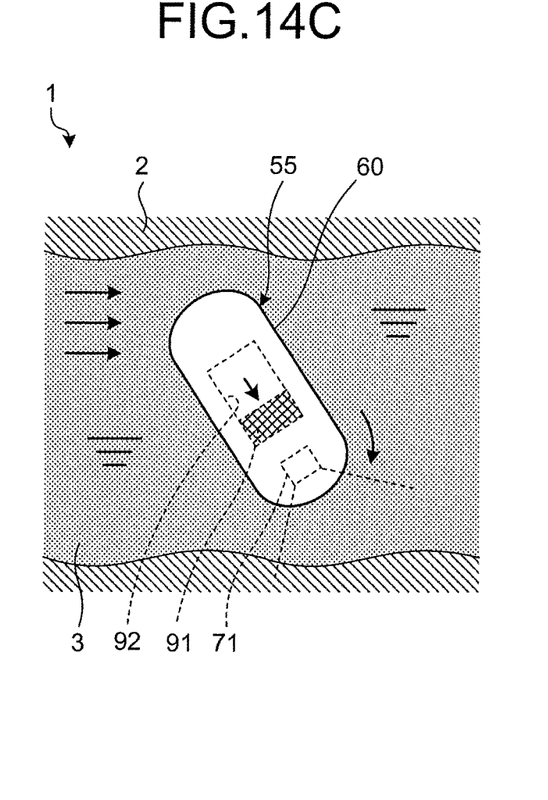

FIGS. 14A to 14C are schematic block diagrams showing a capsule endoscope according to a seventh modification. A capsule endoscope 55 of the seventh modification includes a weight 91 installed in the capsule body 60 and a slide space 92 for sliding the position of the weight 91 in the longitudinal, axial direction of the capsule body 60. Here, the weight 91 slides in the slide space 92 due to the flow of the fluid 3 to the capsule body 60 so that the position of the gravity center of the capsule body 60 is changed.

When the capsule endoscope 55 having such a structure is introduced in the lumen 2 and stays in the fluid 3, for example, the weight 91 is located at a position one-sided in the slide space 92, as shown in FIG. 14A, and the capsule endoscope 55 flows in the fluid 3 in a manner of being tilted due to the position of the gravity center, as shown in FIG. 14A. When the flow of the fluid 3 works on the capsule body 60 in such a condition, the capsule body 60 rotates forwardly to be a substantially horizontal state, as shown in FIG. 14B. With such movement of the capsule body 60, the weight 91 slides to the center of the slide space 92 and further moves to the other end of the slide space 92. According to the dynamical changes of the position of the gravity center, the capsule body 60 moves to continue the rotation, as shown in FIG. 14C. By repeating this operation, the capsule body 60 travels in the lumen 2 due to the flow of the fluid 3 as rotating forwardly. Accordingly, with the capsule endoscope 55 having the structure described in the seventh modification, operations and effects same as those of the second embodiment can be obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical apparatus comprising:
   a capsule body to be introduced into a lumen of a subject, the capsule body having a length in a longitudinal axial direction;
   a control member controlling a movement of the capsule body in the lumen by a flow of a fluid introduced in the lumen; and
   an observing member fixed inside the capsule body and observing a direction of the flow of the fluid and a direction different from the flow of the fluid according to the movement of the capsule body;
   wherein the control member is a rotary guide member which rotates the capsule body in a radial direction about an axis passing through the gravity center of the capsule body and perpendicular to the longitudinal axial direction by the flow of the fluid,
   the rotary guide member includes a pair of one-way resistive elements, the resistive elements having a same shape and being located on an outer surface of the capsule body to be point symmetric with respect to the gravity center of the capsule body in the longitudinal axial direction of the capsule body, and
   one of the pair of one-way resistive elements faces to the flow of the fluid to generate a reaction force.

2. The capsule medical apparatus according to claim 1, wherein the one-way resistive elements are projections.

3. The capsule medical apparatus according to claim 2, wherein the projections can be projected and retracted with respect to the outer surface of the capsule body.

4. The capsule medical apparatus according to claim 2, wherein the projections are pocket projections each having an opening opened along the longitudinal axial direction.

5. The capsule medical apparatus according to claim 1, wherein each of the one-way resistive elements is a groove opened toward an end portion along the longitudinal axial direction.

6. The capsule medical apparatus according to claim 1, wherein each of the one-way resistive elements is a hole opened toward an end portion along the longitudinal axial direction.

7. The capsule medical apparatus according to claim 1, wherein the observing member includes an imaging member which forms an imaging field in the longitudinal axial direction of the capsule body.

8. The capsule medical apparatus according to claim 1, wherein the observing members are respectively fixed at both end portions of the capsule body in the longitudinal axial direction.

9. The capsule medical apparatus according to claim 8, wherein the imaging member includes a first imaging member and a second imaging member, the first imaging member being fixed at an end of the capsule body in the longitudinal axial direction and having a far focus, and the second imaging member being fixed at another end of the capsule body in the longitudinal axial direction and having a near focus.

* * * * *